(12) United States Patent
Uchida et al.

(10) Patent No.: US 8,013,032 B2
(45) Date of Patent: *Sep. 6, 2011

(54) PHOTOPOLYMERIZABLE DENTAL COMPOSITION WITH SUPPRESSED CHANGE IN COLOR TONE BY MONOMER

(75) Inventors: Jun Uchida, Kyoto (JP); Mitsuharu Mizuno, Kyoto (JP); Mitsuji Teramae, Kyoto (JP)

(73) Assignee: Kabushiki Kaisha Shofu, Kyoto (JP)

( * ) Notice: Subject to any disclaimer, the term of this patent is extended or adjusted under 35 U.S.C. 154(b) by 246 days.

This patent is subject to a terminal disclaimer.

(21) Appl. No.: 12/379,925

(22) Filed: Mar. 4, 2009

(65) Prior Publication Data

US 2009/0227699 A1    Sep. 10, 2009

(30) Foreign Application Priority Data

Mar. 4, 2008    (JP) .................. 2008-052963

(51) Int. Cl.
*A61K 6/083* (2006.01)
*C08F 2/48* (2006.01)
*C08F 4/32* (2006.01)

(52) U.S. Cl. .............. 522/64; 522/28; 522/48; 522/173; 522/182; 523/115; 523/116; 433/228.1

(58) Field of Classification Search .............. 522/64, 522/83, 173, 182, 48, 28; 523/115–118; 433/228.1
See application file for complete search history.

(56) References Cited

U.S. PATENT DOCUMENTS

| 4,968,725 | A | * | 11/1990 | Mukai et al. ............. 522/90 |
| 5,320,886 | A | * | 6/1994 | Bowen ............. 428/34.1 |
| 5,519,071 | A | * | 5/1996 | Rheinberger et al. ......... 523/116 |
| 5,530,038 | A | * | 6/1996 | Yamamoto et al. ............ 523/116 |
| 6,730,715 | B2 | * | 5/2004 | Jia ............... 523/115 |
| 7,615,582 | B2 | * | 11/2009 | Nakatsuka et al. ........... 522/171 |
| 2009/0227700 | A1 | * | 9/2009 | Uchida et al. ................. 522/76 |

FOREIGN PATENT DOCUMENTS

WO WO2005/060920  *  7/2005

* cited by examiner

*Primary Examiner* — Susan W Berman
(74) *Attorney, Agent, or Firm* — Wenderoth, Lind & Ponack, L.L.P.

(57) ABSTRACT

Disclosed is a dental composition comprising 0.01 to 10 parts by weight of at least one kind of (a) a visible light-photopolymerization catalyst compound and one or more kinds of (b) di(meth)acrylate compounds represented by the general formula (I):

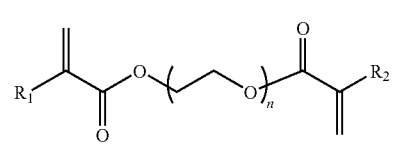

(I)

wherein $R_1$ and $R_2$ each independently represent hydrogen or a methyl group, and a repeating unit number n of an ethylene oxide group is from 9 to 50.

6 Claims, No Drawings

PHOTOPOLYMERIZABLE DENTAL COMPOSITION WITH SUPPRESSED CHANGE IN COLOR TONE BY MONOMER

BACKGROUND OF THE INVENTION

1. Field of the Invention

The present invention relates to a photopolymerizable dental composition which is cured by irradiation with visible light. More particularly, the present invention relates to a dental composition which causes less coloration after curing. The composition of the present invention is used for dental filling materials, dental crown materials, artificial tooth materials, dental adhesives, dental surface coating materials, dental opaque materials, dental manicure materials, etc.

2. Description of the Related Art

Current dental treatments view aesthetic qualities as one of the most important elements. There is a strong requirement for the characteristics of dental materials to be such that the color of restorations resembles that of a natural tooth, and has a beautiful white color.

In actual treatment, a color tone is determined by comparing a color tone of the natural tooth of the patient with that of materials such as fillers. However, materials comprising a combination of a conventionally used visible light-photopolymerization catalyst and a polymerizable monomer displayed inferior aesthetic qualities since a color tone varies before and after curing, resulting in poor compatibility with a color tone after mounting in the oral cavity.

In the dental field, a visible light-polymerizable resin has been widely used. The disclosure of UK Patent No. GB1408265 resulted in broad application of a photopolymerization initiator therefor including a hydrogen abstracting initiator comprising an a-diketone compound and an amine compound, such as camphorquinone having a maximum absorption wavelength of 470 nm. However, a photopolymerization initiator comprising an a-diketone compound and an amine compound has problems such as drastic yellowing and change in a color tone of the cured article associated with the amine compound.

Acylphosphine oxide compounds disclosed in U.S. Pat. Nos. 4,265,723 and 4,298,738, and (bis)acylphosphine oxide compounds disclosed in U.S. Pat. Nos. 4,792,632, 5,721,292 and 5,965,776 show excellent photopolymerizability in an ultraviolet or near ultraviolet range and are therefore widely used in the photopolymerization industry field. Also, these compounds are less likely to cause yellowing of the cured article when compared with an a-diketone compound and an amine compound. However, there is a problem that yellowing is caused by interaction after curing depending on the kind of a polymerizable monomer.

Japanese Patent No. 2,629,060 reports a photopolymerizable dental surface coating material comprising dipentaerythritol hexaacrylate and an acylphosphine oxide compound. This patent reports that the photopolymerizable dental surface coating material has excellent thin-layer surface curability since it contains dipentaerythritol hexaacrylate and an acylphosphine oxide compound. However, there is a problem that curing caused by the dipentaerythritol hexaacrylate and the acylphosphine oxide compound causes browning of the cured article.

SUMMARY OF THE INVENTION

Thus, the present inventors have intensively studied about a combination of a photopolymerization initiator and a radical polymerizable monomer which causes less change in a color tone before and after curing. As a result, surprisingly, we have found that a feature of less change in a color tone before and after curing, suppression of change in a color tone after curing and excellent physical properties are imparted by incorporating a polymerizable monomer represented by the general formula (I):

[Chemical Formula 1]

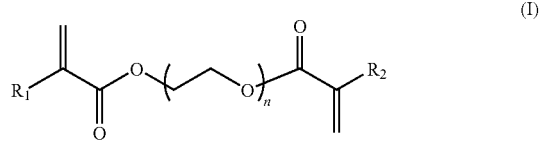

(I)

wherein $R_1$ and $R_2$ each independently represent hydrogen or a methyl group, and a repeating unit number n of an ethylene oxide group is from 9 to 50. Thus, the present invention has been completed.

That is, the present invention provides:

[1] A dental composition comprising 0.01 to 10 parts by weight of (a) at least one kind of a visible light-photopolymerization catalyst compound and (b) one or more kinds of di(meth)acrylate compounds represented by the general formula (I):

[Chemical Formula 2]

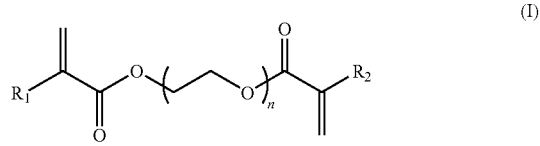

(I)

wherein $R_1$ and $R_2$ each independently represent hydrogen or a methyl group, and a repeating unit number n of an ethylene oxide group is from 9 to 50;

[2] The dental composition according to the above-described [1], wherein (a) the visible light-photopolymerization catalyst compound is an acylphosphine oxide compound;

[3] The dental composition according to the above-described [1] or [2], wherein (a) the visible light-photopolymerization catalyst compound is 2,4,6-trimethylbenzoyldiphenylphosphine oxide;

[4] The dental composition according to any one of the above-described [1] to [3], which further contains (c) a polyfunctional monomer having three or more polymerizable functional groups;

[5] The dental composition according to the above-described [4], wherein (c) the polyfunctional monomer is dipentaerythritol hexaacrylate; and

[6] The dental composition according to the above-described [4] or [5], which contains 5 to 70 parts by weight of (b) the di(meth)acrylate compound and 30 to 95 parts by weight of (c) the polyfunctional monomer.

The photopolymerizable composition which is cured by irradiating with visible light, and a polymerizable monomer used therefor of the present invention cause less change in a color tone before and after curing and cause less change in a color tone after curing, and are also excellent in thin-layer surface curability. The dental composition of the present invention is used for dental filling materials, dental crown materials, artificial tooth materials, veneer crown materials, dental adhesives, dental surface coating materials, dental opaque materials, dental manicure materials, laminate veneers, etc.

DETAILED DESCRIPTION OF THE INVENTION

The present invention will now be described in detail.

Examples of (a) the visible light photocatalyst compound used in the dental composition of the present invention include diacetil, benzil, 4,4'-dimethoxybenzil, 4,4'-dimethoxybenzil, 4,4'-oxybenzil, 4,4'-chlorobenzil, camphorquinone, camphorquinonecarboxylic acid, 2,3-pentadione, 2,3-octadione, 9,10-phenanthrenequionone, acenaphthenequionone, 2,4,6-trimethylbenzoyldiphenylphosphine oxide, 2,6-dimethylbenzoyldiphenylphosphine oxide, 2,6-dimethoxylbenzoyldiphenylphosphine oxide, 2,6-dichlorobenzoyldiphenylphosphine oxide, 2,3,5,6-tetramethylbenzoyldiphenylphosphine oxide, methyl 2,4,6-trimethylbenzbylphenylphosphinate, ethyl 2,4,6-trimethylbenzoylphenylphosphinate, phenyl 2,4,6-trimethylbenzoylphenylphosphinate, etc.

Among these compounds, the acylphosphine oxide compounds show excellent photopolymerizability in an ultraviolet or near ultraviolet range and are therefore widely used in the photopolymerization industry field. The acylphosphine oxide compounds are less likely to cause yellowing of the cured article and also have excellent internal curability. Therefore, the acylphosphine oxide compounds are used for photocuring of transparent thick films and materials containing a pigment having a large hiding power, and have also found recent application in the dental field. The composition using a visible light-polymerization initiator composed of the acylphosphine oxide compound exerts an improved effect of thin-layer surface curability. Therefore, the acylphosphine oxide compound is preferable and 2,4,6-trimethylbenzoyl-diphenylphosphine oxide is more preferable.

The amount of the visible light photocatalyst compound is from 0.01 to 10 parts by weight, preferably from 0.05 to 6 parts by weight, and more preferably from 0.1 to 4.0 parts by weight, based on 100 parts by weight of the after-mentioned radical polymerizable monomer containing (b) a di(meth)acrylate compound and (c) a polyfunctional monomer. When the amount of the acylphosphine compound is less than the above range, thin-layer surface curability deteriorates. In contrast, when the amount of the acylphosphine compound is more than the above range, a yellowish color tone increases and a usable life decreases.

(b) The di(meth)acrylate compound used in the composition of the present invention is a compound represented by the general formula (I):

[chemical formula 3]

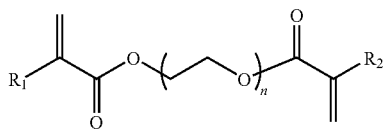

(I)

wherein $R_1$ and $R_2$ each independently represent hydrogen or a methyl group, and a repeating unit number n of an ethylene oxide group is from 9 to 50. The present inventors have found out that change in a color tone before and after curing can be decreased by incorporating the di(meth)acrylate compound in the composition. Since it becomes impossible to suppress change in a color tone when the repeating unit number decreases, it is preferred to use a compound in which the repeating unit number n of the ethylene oxide group is 9 or more. However, when the repeating units excessively increase, stiffness of the cured article disappears and thus the maximum repeating unit number n is preferably less than 50, and preferably less than 23.

Specific examples of (b) the di(meth)acrylate compound used in the composition of the present invention include nonaethylene glycol dimethacrylate, decane ethylene glycol dimethacrylate, undecane ethylene glycol dimethacrylate, dodecane ethylene glycol dimethacrylate, tridecane ethylene glycol dimethacrylate, tetradecane ethylene glycol dimethacrylate, pentadecane ethylene glycol dimethacrylate, hexadecane ethylene glycol dimethacrylate, heptadecane ethylene glycol dimethacrylate, octadecane ethylene glycol dimethacrylate, nonadecane ethylene glycol dimethacrylate, icosane ethylene glycol dimethacrylate, henicosane ethylene glycol dimethacrylate, docosane ethylene glycol dimethacrylate, tricosane ethylene glycol dimethacrylate, tetracosane ethylene glycol dimethacrylate, pentacosane ethylene glycol dimethacrylate, hexacosane ethylene glycol dimethacrylate, heptacosane ethylene glycol dimethacrylate, octacosane ethylene glycol dimethacrylate, nonacosane ethylene glycol dimethacrylate, triacontane ethylene glycol dimethacrylate, tetracontane ethylene glycol dimethacrylate, pentacontane ethylene glycol dimethacrylate, etc.

Further, it becomes possible to remarkably enhance strength characteristics of the composition after curing, such as flexural modulus, hardness, etc., by incorporating (c) the polyfunctional monomer having three or more polymerizable functional groups in the composition of the present invention. Curability is realized to a remarkable degree by adding a polyfunctional monomer. The polyfunctional monomer enables improvement of surface curability and decrease of the surface unpolymerized layer.

Examples of (c) the polyfunctional monomer used in the composition of the present invention include polymerizable polyfunctional acrylate including polyethylenically unsaturated carbamoyl isocyanurates; polymerizable polyfunctional acrylates having an urethane bond, such as phenyl glycidyl ether acrylate hexamethylene diisocyanate urethane prepolymer, phenyl glycidyl ether toluene diisocyanate urethane prepolymer, pentaerythritol triacrylate toluene diisocyanate urethane prepolymer and pentaerythritol triacrylate isophorone diisocyanate urethane prepolymer; ditrimethylolpropane tetraacrylate, ethoxylated pentaerythritol tetraacrylate, propoxylated pentaerythritol tetraacrylate, pentaerythritol tetra(meth)acrylate, dipentaerythritol tetra(meth)acrylate, dipentaerythritol penta(meth)acrylate, dipentaerythritol hexa(meth)acrylate, etc.

Among these monomers, dipentaerythritol hexaacrylate is preferable since it has excellent stability.

It is preferred to add 5 to 70 parts by weight of (b) the di(meth)acrylate compound and 30 to 95 parts by weight of (c) the polyfunctional monomer, in addition to 0.01 to 10 parts by weight of the visible light-photopolymerization catalyst compound so as to decrease change in a color tone after curing and to optimize thin-layer surface curability. When the amount of (b) the di(meth)acrylate compound is too large, curability deteriorates. In contrast, when the amount of (c) the polyfunctional monomer is too large, change in a color tone after curing increases. More preferably, the amount of (b) the di(meth)acrylate compound is from 10 to 50 parts by weight and that of (c) dipentaerithritol hexaacrylate is from 50 to 90 parts by weight.

The dental composition of the present invention can optionally contain a polymerizable monomer as long as the effects of the present invention are not deteriorated. As the polymerizable monomer, known monomers can be used without limitation. Among the polymerizable monomers, examples of the monofunctional monomer compound include ester compounds such as methyl(meth)acrylate, ethyl (meth)acrylate, methoxypolyethylene glycol(meth)acrylate, tetrafurfuryl(meth)acrylate, benzyl(meth)acrylate, phenoxyethyl(meth)acrylate, 2-hydroxyethyl(meth)acrylate, 2-hydroxypropyl(meth)acrylate, 2-hydroxybutyl(meth)acrylate, dimethylaminoethyl (meth)acrylate and 2-(meth)acryloyloxyethyl acid phosphate; styrene-based compounds such as styrene and a-mesitylene; silane compounds such as γ-(meth)acryloxypropyltrimethoxysilane, γ-(meth)acryloxypropyltriethoxysilane, etc.; nitrogen-containing compounds such as 2-(N,N-dimethylamino)ethyl(meth)acrylate, N-methylol(meth)acrylamide, etc.; fluorine-containing compounds such as trifluoroethyl(meth)acrylate, 2,2,3,3,3-pentafluoropropyl (meth)acrylate, etc.; and polymerizable silicone compounds in which the main chain of a polymer is a silicone component and one end is modified with a (meth)acrylate group.

Examples of the difunctional monomer compound include ethylene glycol di(meth)acrylate, diethylene glycol di(meth)acrylate, triethylene glycol di(meth)acrylate, butylene glycol di(meth)acrylate, neopentyl glycol di(meth)acrylate, propylene glycol di(meth)acrylate, 1,3-butanediol di(meth)acrylate, 1,4-butanediol di(meth)acrylate, 1,6-hexanediol di(meth)acrylate, 2,2-bis((meth)acryloxyphenyl)propane, 2,2-bis[4-(3-(meth)acryloxy)-2-hydroxypropoxyphenyl]propane, 2,2-bis(4-(meth)acryloxyethoxyphenyl]propane, 2,2-bis(4-(meth)acryloxydiethoxyphenyl]propane, 2,2-bis(4-(meth)acryloxytriethoxyphenyl]propane, 2,2-bis(4-(meth)acryloxytetraethoxyphenyl]propane, 2,2-bis(4-(meth)acryloxypentaethoxyphenyl]propane, 2,2-bis(4-(meth)acryloxypropoxyphenyl]propane, 2(4-(meth)acryloxydiethoxyphenyl)-2(4-(meth)acryloxydiethoxyphenyl)propane, 2(4-(meth)acryloxydiethoxyphenyl)-2(4-(meth)acryloxytriethoxyphenyl)propane, 2,2-bis(4-(meth)acryloxypropoxyphenyl)propane, 2,2-bis(4-(meth)acryloxyisopropoxyphenyl)propane, 2(4-(meth)acryloxydipropoxyphenyl)-2(4-(meth)acryloxytriethoxyphenyl)propane, etc.

The dental composition of the present invention can properly contain fillers depending on the purpose.

Examples of the filler material include inorganic or organic matter and composites thereof. Examples of the inorganic filler material include soda glass, lithium borosilicate glass, barium glass, strontium glass, zinc glass, fluoroaluminum borosilicate glass, borosilicate glass, crystal quartz, fused silica, synthetic silica, alumina silicate, amorphous silica, glass ceramic, and a mixture thereof. There is no specific limitation on the particle size of the inorganic filler. According to the applications of the composition, fillers having a particle diameter of several nanometers to several tens of nanometers are selected. The inorganic filler is preferably subjected to a conventionally known surface treatment. Examples of the surface treating agent include silane compounds, for example, vinyltrimethoxysilane, vinyltriethoxysilane, vinyltrichlorosilane, vinyltri(β-methoxyethoxy)silane, γ-methacryloxypropyltrimethoxysilane, γ-glycidoxypropyltrimethoxysilane, γ-mercaptopropyltrimethoxysilane, γ-aminopropyltriethoxysilane, etc. As the organic filler, for example, polymer powders of the above polymerizable monomers, and powders (composite fillers) of composites obtained by dispersing inorganic fillers in polymerizable monomers, followed by polymerization can be used.

Further, to the dental composition of the present invention, known components such as polymerization inhibitors, ultraviolet absorbers, pigments, and solvents can be optionally added.

Examples of the polymerization inhibitor include hydroquinone monomethyl ether, butylated hydroxytoluene, hydroquinone, etc. Among these polymerization inhibitors, hydroquinone monomethyl ether and butylated hydroxytoluene are preferable.

Moreover, examples of the ultraviolet absorber include benzophenone-based, cyanoacrylate-based, hindered amine-based and triazine-based compounds, etc.

Moreover, examples of the solvent include water, ethanol, i-propanol, acetone, dimethyl sulfoxide, dimethylformamide, ethyl acetate, butyl acetate, etc.

The present invention relates to a photopolymerizable composition which is cured by irradiating with visible light, and more particularly to a composition with less change in a color tone before and after curing. The composition of the present invention is used for dental filling materials, dental crown materials, artificial tooth materials, dental adhesives, dental surface coating materials, dental opaque materials, dental manicure materials, etc.

Examples

The present invention will now be described in detail by way of Examples and Comparative Examples. The present invention is not limited to these Examples.

Abbreviations of compounds used in Examples of the present invention are as follows.
CQ: dl-camphorquinone
APO: 2,4,6-trimethylbenzoyl-diphenylphosphine oxide
DMBE: Ethyl 4-N,N-dimethylaminobenzoate
DPH: Dipentaerythritol hexaacrylate
UDMA: Dimethacryloxyethyl-2,2,4-trimethylhexamethylene diurethane
23G: Tricosane ethylene glycol dimethacrylate (repeating unit number n=23)
14G: Tetradecane ethylene glycol dimethacrylate (repeating unit number n=14)
9G: Nonaethylene glycol dimethacrylate (repeating unit number n=9)
3G: Triethylene glycol dimethacrylate (repeating unit number n=3)

The procedure for evaluation of materials used in Examples of the present invention is described below.
(1) Evaluation of Thin-Layer Surface Curability A single drop of various photocurable compositions thus prepared was collected on a kneading paper and then spread thinly (thickness: about 0.1 mm) using a hair pencil. After irradiation with light using a halogen lamp irradiator Solidilite [manufactured by SHOFU, INC.] (irradiated for 1 minute), thin-layer surface curability was confirmed by a hand feel.
A: extremely high thin-layer surface curability due to very small amount of unreacted monomer on the surface
B: high thin-layer surface curability due to small amount of unreacted monomer on the surface
C: low thin-layer surface curability due to unreacted monomer on the surface (2) Measurement of Color Difference Before and After Curing Each of various photocurable compositions thus prepared was placed in a stainless steel ring (inner diameter: 15 mm, thickness: 0.5 mm), followed by pressed from a vertical direction using two cover glasses and further colorimetry (L*a*b* colorimetric system) using a spectrocolorimeter CM-2002 (manufactured by Konica Minolta Photo Imaging, Inc.) to give a color tone before curing. In a photopolymerization device (Solidilite, manufactured by SHOFU, INC.), both front and back surfaces of the composition were irradiated with light each for 1 minute and then colorimetry was performed. Color differences ΔE* and Δb* before and after curing were calculated. ΔE* and Δb* are calculated as described below.

$$\Delta E^* = \sqrt{(L_x - L_y)^2 + (a_x - a_y)^2 + (b_x - b_y)^2}$$ [Equation 1]

$$\Delta b^* = |b_x - b_y|$$

$L_x$, $a_x$, $b_x$: Colorimetric value before curing
$L_y$, $a_y$, $b_y$: Colorimetric value after curing Examples 1 to 6 and Comparative Examples 1 to 3

Compositions comprising a visible light-photopolymerization initiator and a radical polymerizable monomer (DPH, 14G) were prepared in a homogeneous solution with each composition shown in Table 1. Evaluation of thin-layer surface curability using a dental light irradiator, evaluation of a color difference before and after curing, and evaluation of a color after curing were performed. The results are shown in Table 1.

TABLE 1

| Components (Parts by weight) and various properties | | Examples | | | | | | Comparative Examples | | |
|---|---|---|---|---|---|---|---|---|---|---|
| | | 1 | 2 | 3 | 4 | 5 | 6 | 1 | 2 | 3 |
| CQ | | — | — | — | — | 1 | — | 1 | 1 | — |
| APO | | 4 | 4 | 4 | 4 | — | 4 | — | — | 4 |
| DMBE | | — | — | — | — | 1 | — | 1 | 1 | — |
| DPH | | 70 | 70 | 70 | — | 70 | — | — | — | 70 |
| 23G | | — | — | 30 | — | — | — | — | — | — |
| 14G | | 30 | — | — | 70 | 30 | 30 | — | — | — |
| 9G | | — | 30 | — | — | — | — | — | — | — |
| UDMA | | — | — | — | 30 | — | 70 | 30 | 70 | — |
| 3G | | — | — | — | — | — | — | 70 | 30 | 30 |
| Thin-layer surface curability | | A | A | A | B | B | B | C | C | C |
| Change of color tone before and after curing | ΔE* | 6 | 7 | 5 | 3 | 6 | 2 | 18 | 16 | 10 |
| | Δb* | 6 | 7 | 5 | 2 | 5 | 2 | 18 | 5 | 9 |

TABLE 1-continued

| Components (Parts by weight) and various properties | | Examples | | | | | | Comparative Examples | | |
|---|---|---|---|---|---|---|---|---|---|---|
| | | 1 | 2 | 3 | 4 | 5 | 6 | 1 | 2 | 3 |
| Color tone after curing | $L_y^*$ | 94 | 92 | 93 | 93 | 94 | 94 | 93 | 95 | 95 |
| | $a_y^*$ | −2 | −2 | −2 | −2 | −11 | −2 | −7 | −4 | −2 |
| | $b_y^*$ | 8 | 10 | 8 | 4 | 29 | 3 | 5 | 10 | 11 |

As is apparent from the results shown in Table 1, the visible light-photopolymerizable compositions (Examples 1 to 6) comprising 0.01 to 10 parts by weight of a visible light photocatalyst compound and a di(meth)acrylate compound of the present invention show excellent thin-layer surface curability, less change in a color tone before and after curing and less color change after curing.

What is claimed is:

1. A dental composition comprising 0.01 to 10 parts by weight of (a) at least one visible light-photopolymerization catalyst compound, 5 to 70 parts by weight of (b) one or more di(meth)acrylate compounds represented by the formula (I):

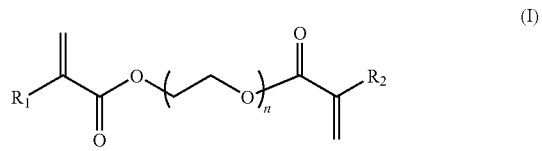

wherein $R_1$ and $R_2$ each independently represent hydrogen or a methyl group, and a repeating unit number n of an ethylene oxide group is from 9 to 50, and 30 to 95 parts by weight of (c) a polyfunctional monomer having three or more polymerizable functional groups.

2. The dental composition according to claim 1, wherein (a) the visible light-photopolymerization catalyst compound is an acylphosphine oxide compound.

3. The dental composition according to claim 2, wherein (a) the acylphosphine oxide compound is 2,4,6-trimethylbenzoyldiphenylphosphine oxide.

4. The dental composition according to claim 3, wherein (c) the polyfunctional monomer is dipentaerythritol hexaacrylate.

5. The dental composition according to claim 2, wherein (c) the polyfunctional monomer is dipentaerythritol hexaacrylate.

6. The dental composition according to claim 1, wherein (c) the polyfunctional monomer is dipentaerythritol hexaacrylate.

* * * * *